United States Patent [19]

Shioyama et al.

[11] Patent Number: 4,560,783

[45] Date of Patent: Dec. 24, 1985

[54] PROCESS FOR PRODUCING ALUMINUM CITRATE SOLUTIONS

[75] Inventors: Tod K. Shioyama; Robert A. Little, both of Bartlesville, Okla.

[73] Assignee: Phillips Petroleum Company, Bartlesville, Okla.

[21] Appl. No.: 544,185

[22] Filed: Oct. 21, 1983

[51] Int. Cl.$^4$ .............................................. C07F 5/06
[52] U.S. Cl. ...................................... 556/183; 556/40
[58] Field of Search ................................. 260/448 R

[56] References Cited

U.S. PATENT DOCUMENTS

| | | | |
|---|---|---|---|
| 3,047,602 | 7/1962 | Schenck | 260/448 R |
| 3,200,136 | 8/1965 | Grossmith | 260/448 B X |
| 3,446,585 | 5/1969 | Tanabe | 260/448 R |
| 3,553,316 | 1/1971 | Rubino | 260/448 B X |
| 3,959,093 | 5/1976 | Merkl | 260/448 R X |
| 4,447,364 | 5/1984 | Staal | 260/448 B X |

OTHER PUBLICATIONS

Kirk—Othmer, Encyclopedia of Chemical Tech., Wiley—Intersc. Publ., John Wiley & Sons, N.Y., 3rd. Ed., vol. 2, pp. 197–209, (1978).

*Primary Examiner*—Helen M. S. Sneed
*Attorney, Agent, or Firm*—E. L. Bowman

[57] ABSTRACT

A process for preparing a stable aqueous solution of aluminum citrate comprising adding citric acid or sodium citrate gradually to an agitated aqueous solution of sodium aluminate under an atmosphere substantially free of carbon dioxide.

13 Claims, 2 Drawing Figures

ALUMINUM CHLORIDE BASED ALUMINUM CITRATE

SODUIM ALUMINATE BASED ALUMINUM CITRATE

PROCESS FOR PRODUCING ALUMINUM CITRATE SOLUTIONS

BACKGROUND OF THE INVENTION

The present invention relates to solutions of aluminum citrate.

Aluminum citrate solutions have been found useful for crosslinking polymers such as carboxymethylcellulose (CMC) or partially hydrolyzed polyacrylamide. The phenomenon has found application in enhanced oil recovery processes. An example of such is disclosed in U.S. Pat. No. 3,762,476. The in situ gelling of the polymers results in blocking of highly permeable zones which can allow one to recover oil which otherwise could not be recovered by conventional means.

In the past, dilute solutions have been prepared in the field by dissolving aluminum sulfate and sodium citrate in water. If the concentration of such solutions is increased, it has been noted that in some formations precipitates form as a result of interaction between the sulfate ions and alkaline earth metal cations in the formation or in the water employed. Such precipitations have been found undesirable since they can result in formation blockages where they are not wanted.

In view of the large quantities of aluminum citrate that are employed in such enhanced oil recovery processes, it is obviously desirable to be able to have available stable, highly concentrated solutions that are substantially free of particulate matter. It is generally desired to have an aluminum citrate solution which, after 100 hours at 100° F., will not contain over about 3 weight percent of solid precipitates. Some such solutions have in the past been made by reacting aluminum chloride, citric acid, and either ammonia or sodium hydroxide.

More recently an alternative method has been discovered for making stable aqueous aluminum citrate solutions from aqueous sodium aluminate and either citric acid or sodium citrate. The technique is disclosed in U.S. patent application Ser. No. 525,911 filed Aug. 24, 1983, the disclosure of which is incorporated herein by reference. When an attempt was made to use this process to make larger batches of the aluminum citrate solutions by using a single reaction of larger quantities of the reactants it was observed that the formation of precipitates was a problem. Since it was known that low reaction temperatures were needed to minimize solid formation, it was concluded that the precipitation occurring during the preparation of larger batches was due to localized heat of reaction. Accordingly, it was concluded that agitation needed to be provided in order to minimize the possibility of localized heats of reaction that could not be dissipated sufficiently by cooling of the reaction mixture. Surprisingly, however, it was discovered that at higher levels of agitation the solids formation problem appeared again.

An object of the present invention is to provide a method for forming large batches of aluminum citrate solutions with a minimal amount of solids formation.

SUMMARY OF THE INVENTION

In accordance with the present invention a stable aqueous solution of aluminum citrate is produced by adding citric acid or sodium citrate gradually to an agitated aqueous solution of sodium aluminate under an atmosphere substantially free of carbon dioxide under suitable reaction conditions followed by neutralization.

DETAILED DESCRIPTION OF THE INVENTION

Figure 1:
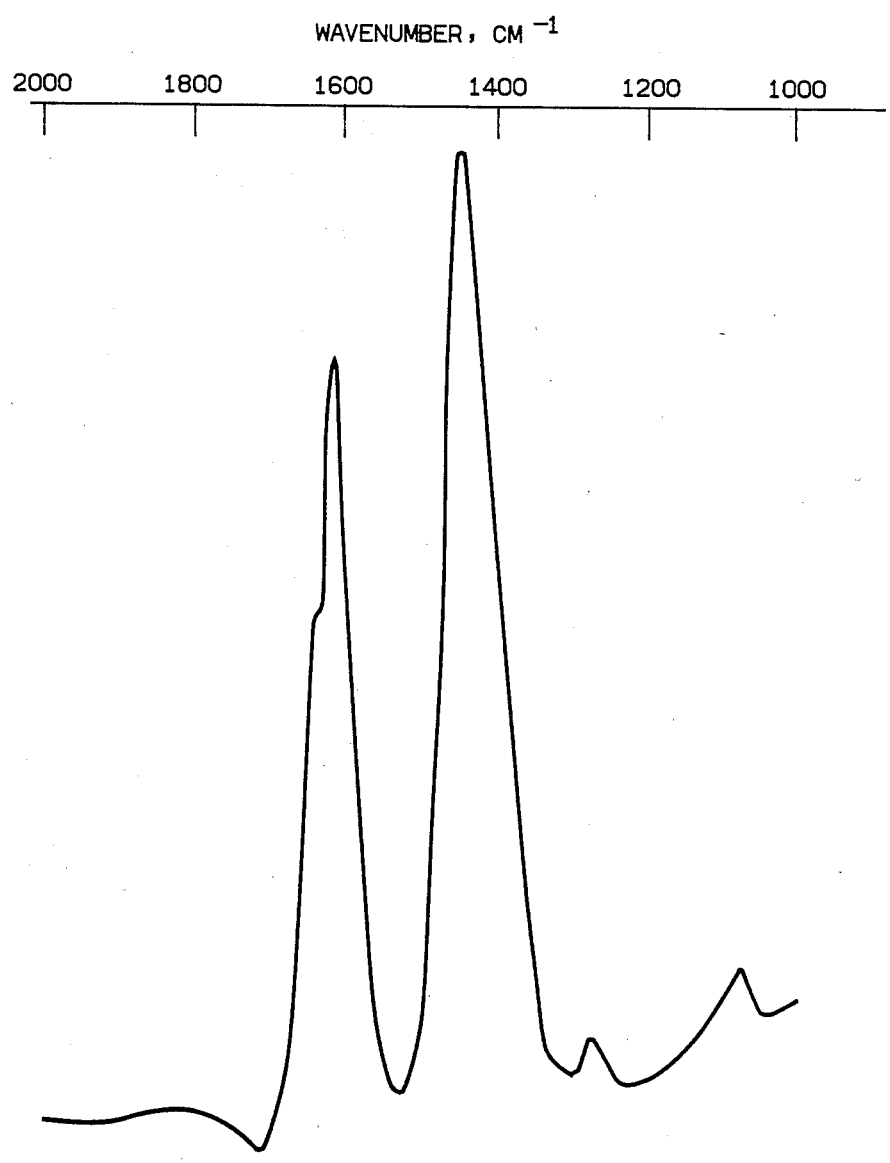
FIG. 1 is a drawing of a portion of the infrared spectrum of a solution of aluminum citrate prepared from aluminum trichloride.

The aqueous solution of sodium aluminate can be obtained in any suitable manner. One alternative involves the dissolution of aluminum metal in aqueous caustic. Another involves the dissolution of solid sodium aluminate in water. Still another alternative involves the reaction of alumina with aqueous caustic. Still another alternative involves the use of commercially available stable aqueous solutions of sodium aluminate.

In view of the fact that it is desirable to obtain a stable concentrated solution of aluminum citrate useful for gelling of CMC or partially hydrolyzed polyacrylamide in enhanced oil recovery, the water employed should preferably be relatively free of ions present in amounts sufficient to result in the formation of any significant amounts of precipitates. The presence of salts can affect the mole ratio of aluminum to citrate that is needed to prevent the aluminum from precipitating and can also affect the time required for the solution to effect gelling of CMC or partially hydrolyzed polyacrylamide solutions. The use of distilled water is, however, not required. Some naturally available water is suitable. The suitability of water sources can be determined by routine evaluation. As a general rule, however, the amount of any single metal in the water should not exceed about 300 ppm. More preferably, water is employed in which no individual metal ion capable of forming insoluble salts is present in an amount greater than 12 parts per million. Water having a total salt content of 1 weight percent or less has generally been found suitable. Generally, it has been found desirable for the aqueous solution of aluminum citrate to contain less than 5 weight percent salt.

When the aqueous solution of sodium aluminate is formed from aluminum metal or alumina, it is preferable to use an excess of caustic in order to minimize the formation of insoluble aluminum hydroxide composition. Typically, the molar ratio of sodium hydroxide to aluminum is at least about 1.25:1. Likewise, if one forms the solution by dissolving solid sodium aluminate in water it is preferable to do so in the presence of a sufficient amount of hydroxyl ions to minimize the formation of insoluble aluminum compounds. While the aluminum citrate of the present invention can be prepared in the presence of foreign solid products, in order for the product to be most acceptable for use in enhanced oil recovery applications, it is best to use sodium aluminate solutions that are substantially free of insoluble solids. Such solutions can be obtained by filtration if necessary.

When the sodium aluminate solution is formed from aluminum metal, it may be desirable to carry out the dissolution in the presence of sodium citrate. The sodium citrate allows one to reduce the amount of sodium hydroxide needed for forming the sodium aluminate solution. When used for this purpose, the molar ratio of sodium citrate to aluminum is generally less than 1/1 and more typically in the range of about 0.1/1 to about 0.6/1. Preferably even when the aluminum is dissolved in the presence of sodium citrate the sodium hydroxide is employed in an amount such that the molar ratio of NaOH to Al is at least about 1/1.

The currently preferred aqueous sodium aluminate solutions are those sold commercially by Nalco Chemical Company. One of these solutions currently identified as 2375 is sold as a product having approximately 41 weight percent $Na_2Al_2O_4$ and about 3.5 weight percent free sodium hydroxide. A more preferred Nalco product currently identified as 2372 is sold as a product having about 32 weight percent $Na_2Al_2O_4$ and about 8 weight percent free sodium hydroxide. Preferably fresh commercial solutions should be used as there is a tendency for neutralization to occur upon standing and such neutralization increases the likelihood of the presence of undesirable solids in the aluminum citrate solution.

For reasons of economics and performance, it is currently preferred to use citric acid rather than sodium citrate. Either can be added as a solid but preferably they are added as an aqueous solution. The temperature at which the citrate and the sodium aluminate are combined can affect the extent to which one obtains a solution substantially free of insoluble solids. Higher temperatures were found to favor the formation of insoluble aluminum hydroxides. Typically the temperature of the reaction medium should be kept below 40° C., preferably below 27° C. and more generally in the range of 7° C. to 24° C.

The agitation of the aqueous solution of sodium aluminate can be provided in any suitable manner. The degree of agitation for optimum results will depend somewhat upon the type and configuration of the reaction vessel and can readily be determined by routine experimentation.

In order to insure that the reaction is conducted under an atmosphere substantially free of carbon dioxide, it is possible to conduct the reaction in a vessel in which substantially all the gases have been evacuated. More preferably, the reaction is simply conducted under an atmosphere of an inert gas. Typical examples of suitable inert gases include nitrogen, argon, helium, and the like.

The mole ratio of aluminum to citrate ion employed can vary over a fairly wide range. Generally, however, that molar ratio should be greater than 1/1 and less than 3/1. Solutions prepared with an aluminum to citrate molar ratio of less than 1.4/1 did not exhibit the ability to gel CMC that would be desired for most enhanced oil recovery processes. The optimum aluminum to citrate molar ratio for solutions to be used as gelling agents has been found to be in the range of about 1.7/1 to about 2/1.

The amount of sodium aluminate employed can vary over a wide range also. However, when amounts are used such that the solution contains around 3.5 weight percent aluminum, the mixture takes on the appearance of a suspension rather than a solution. Thus for the preferred solution, the weight percent of aluminum should be no greater than about 3 weight percent. If more aluminum is used then a stable solution can be prepared by dilution with suitable water.

In order for the solution to remain stable over any significant amount of time, it is necessary to neutralize the product of the citrate and aluminate reaction with a stabilizing amount of a suitable neutralizing agent. Examples of suitable neutralizing agents include inorganic acids and organic acids. Typical acids that have been used include hydrochloric acid, nitric acid, and glacial acetic acid. $AlCl_3$ can be used as the neutralizing agent. The currently preferred neutralizing agent is hydrochloric acid. Neutralizing agents containing multivalent anions, i.e., $SO_4^{-2}$ or $PO_4^{-3}$ are generally not to be used since such anions encourage the formation of insoluble precipitates in well formations. For best results the neutralizing agent should also be added under conditions such that the temperature of the reaction medium remains below 40° C., more preferably below 30° C. The desired level of neutralization generally occurs when the pH has been lowered to a pH in the range of 6 to 9, more typically in the range of 6.5 to 8, and still more typically about 6.5 to 7.

A better understanding of the present invention and its advantages will be provided by reference to the following examples:

EXAMPLE I

The example demonstrates the production of a solution of aluminum citrate using the Nalco Chemical Company sodium aluminate solution which was sold as containing 41 weight percent $Na_2Al_2O_4$. One hundred grams of the sodium aluminate solution was added to a beaker located in an ice bath. Then 45.24 grams of citric acid dissolved in 300 ml of distilled water was slowly added to the sodium aluminate while the mixture was stirred under an air atmosphere. Addition rate was controlled so that the temperature of the mixture never exceeded 20° C.

The solution turned white upon addition of the citric acid. After all the citric acid was added the pH was adjusted to 6.8-7.0 with concentrated HCl. Noticeable amounts of precipitate were present.

An identical preparation carried out under nitrogen rather than air yielded a clear solution free of precipitate. The solution was then diluted with 502 grams of distilled water for storage and testing as a gelling agent for CMC.

Figure 2:
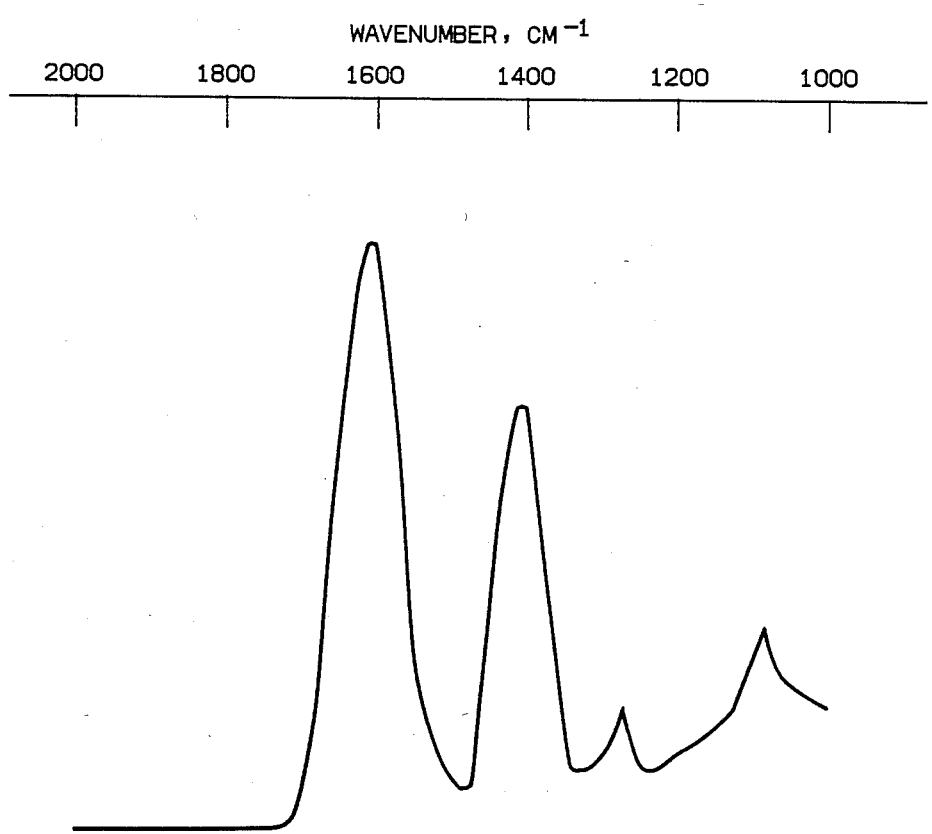
FIG. 2 is a drawing of a portion of the infrared spectrum of a solution of aluminum citrate prepared in accordance with the present invention.

Products prepared in accordance with the present invention subjected to Fourier transform infrared adsorption spectroscopy using distilled water as the reference solution reveal a spectrum of the type shown in FIG. 2. The tallest adsorption peak is located in the range of about 1550 cm$^{-1}$ to about 1650 cm$^{-1}$. The next tallest adsorption peak is located in the range of 1350 to 1450 cm $^{-1}$. This is in contrast to the spectrum obtained using the same analysis technique on the prior art aluminum citrate solutions prepared from aluminum chloride. The aluminum chloride based solutions have a spectrum as shown in FIG. 1, wherein the tallest adsorption peak is at about 1440 cm$^{-1}$ and the next tallest adsorption peak is at about 1610 cm$^{-1}$.

The suitability of the solution prepared under nitrogen as a gelling agent for carboxymethylcellulose was evaluated using a CMC solution prepared by adding 5 g of CMC to 1 liter of deionized water while stirring. Ten grams of potassium chloride as then dissolved and the pH adjusted to 3.6 with concentrated HCl. The gel test involved adding 1 ml of the aluminum citrate solution to 30 ml of the CMC solution, shaking for 30 seconds and then noting how long it took until the material took on a jelly-like texture. The diluted aluminum citrate prepared using sodium aluminate and a $N_2$ atmosphere caused gelling in less than a minute.

The process of the present invention has been used to make batches of aluminum citrate containing about 3 weight percent aluminum as large as 772 gallons.

What is claimed is:

1. A process for preparing a stable aqueous solution of aluminum citrate comprising adding citric acid or sodium aluminate under an atmosphere substantially free of carbon dioxide under suitable reaction conditions below 40° C. followed by neutralization.

2. A process according to claim 1 wherein the neutralization is to a pH in the range of 6 to 9.

3. A process according to claim 2 wherein the citrate and the sodium aluminate are combined at a temperature below 40° C. and wherein the neutralization is conducted at a temperature below 40° C.

4. A process according to claim 3 wherein the mixing of the citrate and the sodium aluminate is conducted under an atmosphere of an inert gas.

5. A process according to claim 4 wherein the inert gas consists essentially of nitrogen.

6. A process according to claim 5 wherein the molar ratio of aluminum to citrate is in the range of 1.4/1 to 2.3/1.

7. A process according to claim 6 which yields an aqueous solution wherein the tallest absorption peak in the area bounded by wave numbers 2000 $cm^{-1}$ and 1000 $cm^{-2}$ in the infrared absorption spectrum of the solution obtained using Attenuated Total Reflectance Fourier transform infrared spectroscopy with distilled water as the reference solution is in the range of 1550 $cm^{-1}$ to 1650 $cm^{-1}$.

8. A process according to claim 7 wherein citric acid is employed.

9. A process according to claim 8 wherein said citric acid is added to said aqueous sodium aluminate solution in the form of an aqueous solution.

10. A process according to claim 5 wherein said citric acid is added to said aqueous sodium aluminate solution in the form of an aqueous solution.

11. A process for minimizing the formation of solids during the formation of an aqueous solution of aluminum citrate from sodium aluminate and citric acid or sodium citrate when the molar ratio of aluminum to citrate is greater than 1/1 comprising adding citric acid or sodium citrate gradually to an agitated aqueous solution of sodium aluminate under an atmosphere substantially free of carbon dioxide under suitable reaction conditions below 40° C. followed by neutralization.

12. A process according to claim 11 wherein the neutralization is to a pH in the range of 6 to 9.

13. A process according to claim 1 wherein the molar ratio of aluminum to citrate in the reactants is greater than 1/1.

* * * * *

UNITED STATES PATENT AND TRADEMARK OFFICE
CERTIFICATE OF CORRECTION

PATENT NO. : 4,560,783

DATED : December 24, 1985

INVENTOR(S) : Tod K. Shioyama; Robert A. Little

It is certified that error appears in the above—identified patent and that said Letters Patent is hereby corrected as shown below:

Claim 1 should read as follows:

1. A process for preparing a stable aqueous solution of aluminum citrate comprising adding citric acid or sodium citrate gradually to an agitated aqueous solution of sodium aluminate under an atmosphere substantially free of carbon dioxide under suitable reaction conditions below 40°C followed by neutralization.

Signed and Sealed this

Twenty-ninth Day of April 1986

[SEAL]

Attest:

DONALD J. QUIGG

Attesting Officer    Commissioner of Patents and Trademarks